United States Patent [19]
Humbert et al.

[11] 3,988,435
[45] Oct. 26, 1976

[54] DIHYDROCHALCONE GLYCOSIDE DERIVATIVES AND PHARMACEUTICAL COMPOSITIONS CONTAINING SAME

[75] Inventors: Francoise Ernestine Lucie Humbert, Paris; Robert Dedieu, Courbevoie, both of France

[73] Assignee: Lever Brothers Company, New York, N.Y.

[22] Filed: Jan. 9, 1974

[21] Appl. No.: 431,826

[30] Foreign Application Priority Data
Jan. 12, 1973  Luxemburg............................ 66823

[52] U.S. Cl.................................. 424/54; 424/48; 424/64; 424/180; 426/590; 426/599; 426/653; 426/658; 536/8
[51] Int. Cl.² .................... A61K 7/22; C07H 17/04
[58] Field of Search..................... 260/210 F, 210 R; 424/54, 180

[56] References Cited
UNITED STATES PATENTS

| | | | |
|---|---|---|---|
| 3,087,821 | 4/1963 | Horowitz et al................ | 260/210 F |
| 3,375,242 | 3/1968 | Horowitz et al................ | 260/210 F |
| 3,429,873 | 2/1969 | Horowitz et al................ | 260/210 F |
| 3,654,261 | 4/1972 | Johnson......................... | 260/210 R |

*Primary Examiner*—Johnnie R. Brown
*Attorney, Agent, or Firm*—James J. Farrell; Kenneth F. Dusyn; Melvin H. Kurtz

[57] ABSTRACT

Dihydrochalcone glucosides are reacted with certain quaternary ammonium compounds to give the corresponding quaternary ammonium derivatives. These new derivatives have a sweet taste and are bactericidal in nature: they can be used in oral products such as dentifrice.

11 Claims, No Drawings

DIHYDROCHALCONE GLYCOSIDE DERIVATIVES AND PHARMACEUTICAL COMPOSITIONS CONTAINING SAME

The present invention concerns a group of novel compounds having a bactericidal effect and a sweet taste, which can be used in compositions for the care of the mouth which are meant to retard or to prevent the formation of dental plaque and calculus and thereby reduce the incidence of gingival disease and caries.

More particularly the invention is concerned with the chemical combination of quaternary ammonium derivatives with dihydrochalcones.

The quaternary ammonium derivatives are classified as cationic compounds having a bactericidal activity. Those with long chains are surfactants and are used in hair-care products, in the food industry, in medicine as disinfectants etc. Although, in certain formulations, when mixed with nonionics, they are barely toxic and irritating, their very bitter taste makes it difficult to apply them in food products and for use in the mouth as anti-plaque and-caries substances.

The object of this invention is to prepare germicidal compounds of little toxicity, little irritation and sweet taste. Furthermore, the invention is concerned with their use in food products and in particular in products for the care of the mouth.

The quaternary ammonium compounds are used as anti-caries substances because it is believed that the initiation of the caries is produced by interplay of bacteria and a carbohydrate substrate in contact with a susceptible surface. This interaction takes place within the dental plaque which adheres to the tooth surface.

In the second phase, the plaque undergoes gradual calcification to form dental calculus. It is not known what initiates this calcification process. Bacteria must play a role in some way.

The presence of calculus in all of the forms of periodontal pathology seems to indicate that calculus is a prime cause of the disease process. Calculus does not only act as a mechanical irritant to the gingival tissues, with its superficial layer of bacterial plaque, it also serves to extend the bacteria and their toxic products to the gingival culculus epithelium.

Applicants have already described in an earlier patent application quaternary ammonium alkylphosphates for the care of the mouth which retard the formation of plaque and calculus. These compounds, just like the quaternary ammonium compounds, tend to inhibit the growth of or kill the micro-organisms in the oral activity. However, these germicides do not combine all the necessary properties. Often they are not sufficiently substantive on the teeth and their taste is sometimes very bitter. For this reason there is some hesitation about using them in practice.

According to the present invention the compositions for the care of the mouth that are suitable to lessen the formation of the dental plaque, tartar and calculus comprise, besides a suitable carrier, one or more of the novel salts of dihydrochalcones wherein the anion is a dihydrochalcone having a sweet taste and the cation is a quaternary ammonium as bactericides and essential active constituents.

These novel compounds have a good bactericidal effect, they are sufficiently substantive and have a hardly perceptible bitter taste, probably because of the sweet taste of the dihydrochalcone part.

The dihydrochalcones have been proposed for many years as food sweetners. Their properties and methods of preparation are described in patent specifications and in literature (e.g. U.S. Pat. Nos. 3,087,821, 3,364,126, 3,625,700, J. Agr. Food Chem. 16, 108 (1968).

The chemical combination of the dihydrochalcones with the quaternary ammoniums, whether by neutralisation reaction starting from the free quaternary base or by double decomposition starting from quaternary ammonium halogenide, does not give difficulties.

Typical examples of quaternary ammonium derivatives suitable for the synthesis of the compounds of the invention are the alkyl trimethyl ammonium halogenides of the formula $R - N(CH_3)_3X$ and the alkyl benzyl dimethyl ammonium halogenides of the formula $R - N(CH_3)_2.CH_2C_6H_5.X$, in which X represents chlorine, bromine or fluorine and R represents an alkyl radical with 8 to 18 carbon atoms. Other suitable compounds are the alkyl dimethyl benzyl ammonium halogenides, the benzyl radical of which has as substituents one or more chains of 1 to 4 carbon atoms, a methyl radical, two methyl radicals, an ethyl radical, alkyldimethyl-naphthyl ammonium halogenides etc.

Various other similar compounds are also suitable, such as e.g. N-alkylpyridinium halogenides and N-trialkyl cyclohexanol ammonium halogenides.

Quaternary ammonium derivatives suitable for the preparation of dihydrochalcone salts are e.g. tetradecyl trimethyl ammonium bromide, hexadecyl trimethyl ammonium bromide and benzyl dimethylalkyl ammonium halogenides such as benzyl dimethyl tetradecyl ammonium chloride.

The novel compounds of the invention are represented by the following general formula:

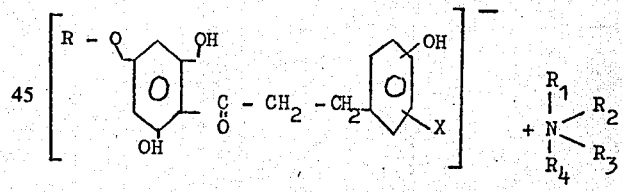

in which
R is a glucosyl or neohesperidosyl radical,
X is H, OH, $OCH_3$, $OC_3H_7$,
$R_{1-3}$ is a straight or branched chain, saturated or unsaturated alkyl radical having 1 to 30 carbon atoms, in which two or three radicals can be combined in such a way that the nitrogen forms part of a cycle, e.g. pyridin, piperidin, or morpholin,
$R_4$ is alkyl, hydroxyalkyl, $C_{7-30}$ aralkyl, aryl, cyclohexyl, cyclohexanol, a cyclic nitrogen-containing radical, or naphthyl.

Of the preferred group of quaternary ammonium derivatives according to the invention, the neohesperidin dihydrochalcone and the naringin dihydrochalcone derivatives can be mentioned such as tetradecyl trimethyl ammonium neohesperidin dihydrochalcone, tetradecyl trimethyl ammonium naringin dihydrochalcone, tetradecyl dimethyl benzyl ammonium neohesperidin dihydrochalcone, dodecyl dimethyl naphthylmethyl ammonium naringin dihydrochalcone and tetradecyl pyridinium neohesperidin dihydrochalcone.

The compounds according to the invention can be used in efficient and sufficient quantity in products in which a bactericidal effect is desired, more particularly in products wherein little toxicity, little irriation and a sweet taste are desired. They can also be used in products for the care of the mouth, such as dentifrices in paste or powder form, in mouth washes, chewing gums, gargles, nose drops, tooth-picks, lipsticks, gums for stamps, labels and envelopes. They can also be used in food products, such as drinks, fruit juices, jams, bakery products, dairy products, sweeteners etc.

In the dentifrices the germicidal sweetening quaternary ammonium dihydrochalconates can be used with nonionic, amphoteric or weakly ionisable products.

The dentifrices according to the invention meet the requirements of good dentifrices as far as taste, cleaning effect, foaming power etc. are concerned. They have an excellent effect on plaque. As abrasives that are compatible with the quaternary ammonium dihydrochalconates, use can be made of metallic compositions usually applied for this purpose, such as e.g. silica, silicates, silicon oxides, aluminium compounds such as hydrated aluminium oxides; aluminium and sodium silicates, thermosetting resins, resins of formaldehyde urea or melamine formaldehyde urea, etc.

For application in the products according to the invention, the silica-xerogels described in U.S. Pat. No. 3,538,230 are e.g. suitable. They are obtained from Grace Davison Chemical, U.S.A. and Joseph Crosfield & Sons Ltd., England.

Preferably the pulverized alpha-alumina trihydrate described in French patent specification No. 1,559,196 is used.

The abrasives can be used in the usual quantities, which are generally about 32 to 75%, preferably 40 to 55%. E.g. at least 20 wt.% of an abrasive is used, at least 30 wt.% of which consists of pulverized alpha-alumina trihydrate having a particle size such that at least 30 wt.% of the particles have a size larger than 20 microns.

Preferably the above-mentioned pulverized alpha-alumina trihydrate is used as the sole abrasive.

Surface-active agents suitable for use include polyoxyethylene esters, e.g. polyoxyethylene stearate, polyoxyethylene monolaurate, sucrose esters, polyoxyethylene sorbitan esters, derivatives of fatty amines with betaine structures (e.g. dehytones produced by Henkel), amine oxides and ethers of polyethyleneglycols and linear alcohols (e.g. certain tergitols produced by Union Carbide). Of these compounds the monolaurate and polyoxyethylene sorbitan monostearate are preferred.

A typical dentifrice according to the invention comprises 1 to 2.5 wt.% of a foaming agent.

As swelling agents, gelling agents or thickening agents, hydroxyalkylcelluloses (e.g. methyl, ethyl or propyl), polyethylene glycols, polypropylene glycols, polyvinylpyrrolidene, aerosils and bentonites, vegetable mucilages such as viscarin can be mentioned.

In general the content of this swelling agent is 1 to 10 wt.% or more of the total composition, and preferably 0.2 to 5 wt.%

Hydroxy ethyl cellulose is particularly suitable. The usual compositions of dentifrices also comprise sweeteners. As quaternary ammonium dihydrochalconate is both germicide and sweetener, addition of other sweeteners, such as e.g. sodium saccharinate, is not necessary.

The content of sweetening germicide agent in the compositions according to the invention is generally 0.01 to 5 wt.% of the total composition. Besides, bleaching agents such as titanium dioxide, optical brighteners, humectants, such as polyhydric alcohols, e.g. sorbitol, mannitol, glycerin, inositol, propylene glycol; film-forming substances, such as silicones, harmless colouring substances, flavours, flavour-retaining or -enhancing agents, nonionic or weakly ionisable, can also be incorporated in the toothpastes according to the invention.

It stands to reason that according to the foregoing description the derivatives of the invention and their mixtures can be used in a large number of products that are ingested, consumed or otherwise perceived organoleptically.

The following Examples are given to illustrate the methods of preparing the compounds of the invention and their application. It will be understood that these Examples are given merely for illustrative purposes without, however, being limited thereto.

Unless otherwise indicated, all parts, percentages, ratios and proportions in the present application are by weight.

EXAMPLE I

Preparation of tetradecyl trimethyl ammonium neohesperidin dihydrochalcone 400 g (1.2 mole) tetradecyl trimethyl ammonium bromide are dissolved in 1.5 l pure ethanol; 69 g dissolved potassium are added to pure ethyl alcohol. The precipitating potassium bromide is removed by filtration. Strength in hydroxide = 0.582 N; Bromide 0.64%; Sulphuric ashes 0.85%.

700 g (1.2 mole) neohesperidin dihydrochalcone are suspended in ethanol and added to the solution of noramium hydroxide.

The clear solution thus obtained is diluted with two times its volume of water.

The crystalline precipitate formed is separated by filtration and dried.

In this way 820 g tetradecyl trimethyl ammonium neohesperidin dihydrochalcone are obtained. This product is in the form of light yellow crystals that decompose before melting. Yield 80%.

The purity is determined by titration of the bound quaternary ammonium, expressed in milliequivalent for 100 g product.

Calculated—117.9. Found—119.

EXAMPLE II

Preparation of tetradecyl trimethyl ammonium neohesperidin dihdyrochalcone 5 g neohesperidin dihydrochalcone are dissolved in 20 ml water, to which 8.4 meq soda are added. 2.85 g tetradecyl trimethyl ammonium bromide dissolved in 20 ml water are added. After standing, the crystals of tetradecyl trimethyl ammonium neohesperidin hydrochalcone are filtered and dried.

In this way 5 g of crystals are obtained. Yield 75%.

The purity is determined by titration of the bound quaternary ammonium, expressed in milliequivalent for 100 g product.

Calculated — 103.2, Bromine = 0. Found — 103.2, Sodium = 0.

EXAMPLE III

Preparation of dodecyl dimethyl naphthyl ammonium naringin dihydrochalcone

An ethanolic suspension of 5 g (8.7 meq) narigin dihdrochalcone is neutralised by an ethanolic solution (8.7 meq) of dodecyl dimethyl naphthyl-1-methyl ammonium hydroxide. The clear solution is then evaporated.

The purity is determined by titration of the bound quaternary ammonium expressed in milliequivalent for 100 g product.

Calculated — 117. Found — 123.5.

The ethanolic solution of dodecyl dimethylnaphthyl ammonium hydroxide is obtained starting from an ethanolic solution of dodecyl dimethyl naphthyl ammonium bromide by means of ion exchange.

Strength in dodecyl dimethyl naphthyl ammonium hydroxide = 0.066 N.

The bactericidal effectiveness is evaluated by means of the minimum inhibitory concentration test in which the lowest concentration of the microbiologically active compound is determined which inhibits the growth of the micro-organisms chosen. This is a technique known to those skilled in the art.

Test tubes containing 9 ml of medium of Jordan are prepared using (1) 2% sucrose, (2) blood serum and (3) 0.4% mucin. The compound of the invention is added to a suitable concentration in the test tubes. The tubes are then inoculated with 0.2 of a 24 hours old culture of streptococcus Ingbritt 00101, incubated at 37°C for 48 hours, after which the development of the culture is observed. The results of the tests are shown in Table I.

Table I

| | Minimum inhibitory concentration | | |
|---|---|---|---|
| | Media | | |
| Compounds | Jordan % | Jordan + serum % | Jordan + mucin % |
| Tetradecyl trimethyl ammonium neohesperidin dihydrochalcone | 0.003 | 0.03 | 0.006 |
| Tetradecyl trimethyl ammonium naringin dihydrochalcone | 0.003 | 0.03 | 0.003 |

Table I-continued

| | Minimum inhibitory concentration | | |
|---|---|---|---|
| | Media | | |
| Compounds | Jordan % | Jordan + serum % | Jordan + mucin % |
| Tetradecylpyridinium neohesperidin dihydrochalcone | 0.003 | 0.03 | 0.03 |
| Tetradecyl dimethylbenzyl ammonium neohesperidin dihydrochalcone | 0.003 | 0.03 | 0.006 |
| Dodecyldimethyl naphthylmethyl ammonium naringin dihydrochalcone | 0.003 | 0.03 | 0.03 |
| Tetradecyl trimethyl ammonium bromide (NORAMIUM M 14) | <0.0003 | 0.006 | 0.006 |

From Table I it will be seen that the bactericidal activity of the compounds according to the invention is generally weaker than that of tetradecyl trimethyl ammonium bromide used as reference. But this activity is completely satisfactory and sufficient for their use in products for the care of the mouth.

The organoleptic tests were carried out in a 0.2% aqueous or hydroalcoholic solution. The tastes of certain compounds are stated in Table II and compared with the taste of tetradecyl trimethyl ammonium bromide.

The organoleptic test was carried out by an expert, who noted the time during which the bitter and sweet taste was perceived.

Table II

| | Organoleptic evaluation | | |
|---|---|---|---|
| Compounds | Physical form of compound | Bitter taste | Sweet taste |
| Tetradecyl trimethyl ammonium neohesperidin dihydrochalcone | 0.2 % aqueous suspension | 30 first sec. Medium; None after 1 min. | 5 first min. strong; medium for 20'; weakens after 25' |
| Tetradecyl trimethyl ammonium naringin dihydrochalcone | 0.2 % aqueous solution | 1st min.: strong with sourness; weakens after 2 min. | 7 first min. medium; weak for 20'; weakens after 25' |
| Tetradecyl pyridinium neohesperidin dihydrochalcone | 0.2 % aqueous solution | 1st minute weak; weakens after 2' | 4 first min. strong; medium for 10'; weakens after 15' |
| Tetradecyl dimethyl benzyl ammonium neohesperidin dihydrochalcone | 0.2 % aqueous solution | first minute weak; weakens after 2' | 6 first min. strong; medium for 10'; weakens after 16' |
| Dodecyl trimethyl naphthylmethyl ammonium naringin dihydrochalcone | 0.2 % hydroalcoholic solution | 3 first min. medium; weakens after 4' | 5 first min. medium; weakens after 12' |
| Tetradecyl trimethyl ammonium bromide | 0.2 % aqueous solution | immediately very strong | — |

It was observed that the compounds developed a very light and transient bitter taste that is masked very quickly by the appearance of a very persistent sweet taste.

Table III shows the relative sweetness of different compounds of the invention as compared with sucrose. The sweetening power with respect to sucrose was determined by comparing the thresholds of identification of the sweet taste of the various sweetening bacteridide with that of sucrose. The numbers in the Table show the results obtained by 20 testers.

Table III

| | Sweetening power | |
|---|---|---|
| | Thresholds % by weight | Content of sweetness |
| Sucrose | 0.40 | 1 |
| Tetradecyl trimethyl ammonium neohesperidin dihydrochalcone | 0.0005 | 800 |

Table III-continued

| Sweetening power | Thresholds % by weight | Content of sweetness |
|---|---|---|
| Tetradecyl trimethyl ammonium naringin dihydrochalcone | 0.02 | 20 |
| Tetradecyl pyridinium neohesperidin dihydrochalcone | 0.0005 | 800 |
| Tetradecyl dimethylbenzyl ammonium neohesperidin dihydrochalcone | 0.00025 | 1600 |
| Dodecyl dimethyl naphthylmethyl ammonium neohesperidin dihydrochalcone | 0.005 | 800 |

The irritation on the skin was tested on rabbits by means of the Ligett subcutaneous injection method. In this test 0.5 to 0.01% solutions of the compound to be examined are injected at different places into the shaven skin of several laboratory rabbits (in general four for each compound). After 24–48, or 72 hours if there was no reaction, the irritation of the skin is determined and expressed as a number. The following reactions were noted: (a) erythema, (b) oedema, (c) dryness, (d) cracking, (e) peeling.

The numerical value corresponding to each case is (a) 0.15 (doubtful reaction), (b) 0.25 (very slight reaction, (c) 0.5 (slight reaction), (d) 1 (visible reaction), (e) 2 (distinct reaction) and 3 (very serious reaction).

The investigation of the irritation of the products tested is carried out parallel with Victamin C (lauryl ammonium-N-lauryl-0-ethyl-phosphoramidate ex Stauffer Chemical Corp.), which compound is taken as reference. The results are expressed in ratios.

$$R = \frac{\text{Irritation owing to the compound}}{\text{Irritation owing to Victamin C}}$$

| Compounds | R |
|---|---|
| Tetradecyl trimethyl ammonium bromide (NORAMIUM 14) | 1.16 |
| Tetradecyl trimethyl ammonium, neohesperidyl dihydrochalcone | 0.025 |
| Tetradecyl trimethyl ammonium, naringin dihydrochalcone glucoside | 0.57 |
| Tetradecyl pyridinium, neohesperidin dihydrochalcone | 0.62 |

EXAMPLE IV

| DENTIFRICE | % |
|---|---|
| Alumina | 43 |
| Water | 22.5 |
| Viscarine | 1.3 |
| Glycerine | 15 |
| Sorbitol (90 %) | 16 |
| Tween 20 | 0.5 |
| Flavour | 1.2 |
| Tetradecyl trimethyl ammonium neohesperidin dihydrochalcone | 0.5 |

EXAMPLE V

| DENTIFRICE | % |
|---|---|
| Calcium carbonate | 20 |
| Dicalcium phosphate | 28 |
| Sorbitol (70 %) | 20 |
| Viscarine | 1.5 |
| Tween 20 | 0.5 |
| Flavour | 1.1 |
| Dodecyl dimethyl naphthylmethyl ammonium, naringin dihydrochalcone | 0.5 |
| Water | 28.4 |
| pH = 9 | |

EXAMPLE VI

| DENTIFRICE | % |
|---|---|
| Dicalcium phosphate | 50 |
| Monosodium phosphate | 5 |
| Disodium phosphate | 2 |
| Viscarine | 1.3 |
| Sorbitol (70 %) | 10 |
| Glycerine | 5 |
| Tetradecyl pyridinium, neohesperidin dihydrochalcone | 0.5 |
| Tween 60 | 0.5 |
| Flavour | 1.2 |
| Water | 24.5 |

EXAMPLE VII

| MOUTH WASH | % |
|---|---|
| Tetradecyl dimethyl benzyl ammonium neohesperidin dihydrochalcone | 0.1 |
| Sorbitol (70 %) | 20 |
| Distilled water | 49.499 |
| Tween 60 | 0.3 |
| Bugarian mint oil | 0.05 |
| Ceylon cinnamon oil | 0.05 |
| Red No. 2 (FD & C) | 0.001 |
| Alcohol B.G. 95 % | 30 |
| pH = 9 | |

EXAMPLE VIII

| DENTIFRICE | % |
|---|---|
| Alumina | 43 |
| Water | 22.5 |
| Hydroxy methyl cellulose | 1.3 |
| Glycerin | 15 |
| Sorbitol (90 %) | 16 |
| Tween 20 | 0.5 |
| Flavour | 1.2 |
| Tetradecyl trimethyl ammonium neohesperidin dihydrochalcone | 0.5 |
| pH = 8.8 | |

EXAMPLE IX

| DENTIFRICE | % |
|---|---|
| Calcium carbonate | 20 |
| Dicalcium phosphate | 28 |
| Sorbitol (70 %) | 20 |
| Hydroxy methyl cellulose | 1.5 |
| Tween 20 | 0.5 |
| Flavour | 1.1 |
| Dodecyl dimethyl naphthyl methyl ammonium naringin dihydrochalcone | 0.5 |
| Water | 28.4 |
| pH = 8 | |

EXAMPLE X

| DENTIFRICE | % |
|---|---|
| Dicalcium phosphate | 50 |
| Hydroxy methyl cellulose | 1.3 |
| Sorbitol (70 %) | 10 |
| Glycerin | 5 |
| Tetradecyl pyridinium neophesperidin dihydrochalcone | 0.8 |
| Tween 60 | 0.5 |
| Flavour | 1.2 |
| Water | 31.2 |
| pH = 7.7 | |

What is claimed is:

1. Dihydrochalcone derivatives having the structure:

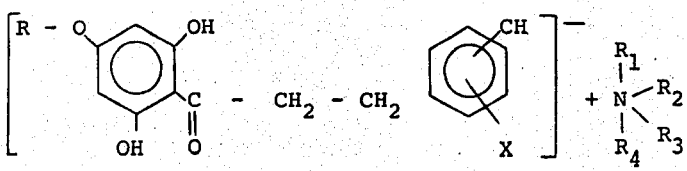

in which
R is a glucosyl or neohesperidosyl radical
X is H, OH, $OCH_3$, or $OC_3H_7$
$R_1$, $R_2$, and $R_3$ are each straight or branched chain, saturated or unsaturated alkyl radicals having 1 to 30 carbon atoms, or in which two or three of said $R_1$, $R_2$ and $R_3$ radicals taken together with said nitrogen forms a heterocyclic ring structure selected from the group consisting of pyridine, piperidine or morpholine, and in which
$R_4$ is alkyl, hydroxyalkyl, $C_{7-30}$ aralkyl, aryl, cyclohexyl, cyclohexanol, or piperidyl.

2. Dihydrochalcone derivatives having the structure:

in which
R is neohesperidosyl
X is H or $OCH_3$
$R_1$ is $C_{12}$ or $C_{14}$ alkyl
$R_2$ is $CH_3$, benzyl or methyl naphthyl.

3. Tetradecyl trimethyl ammonium neohesperidin dihydrochalcone.
4. Tetradecyl trimethyl ammonium naringin dihydrochalcone.
5. Tetradecyl dimethyl benzyl ammonium neohesperidin dihydrochalcone.
6. Dodecyl dimethyl naphthylmethyl ammonium naringin dihydrochalcone.
7. Tetradecyl pyridinium neohesperidin dihydrochalcone.
8. A bactericidal composition comprising a carrier and about 0.1 to about 5.0% by weight of said composition of a dihydrochalcone derivative according to claim 2.
9. A dentifrice comprising a carrier and about 0.1 to about 5.0% by weight of said composition of a dihydrochalcone derivative according to claim 2.
10. A bactericidal composition comprising a carrier and about 0.1 to about 5.0% by weight of said composition of a dihydrochalcone derivative according to claim 1.
11. A dentifrice comprising a carrier and about 0.1 to about 5.0% by weight of said composition of a dihydrochalcone derivative according to claim 1.